United States Patent [19]
Rose, Jr.

[11] Patent Number: 5,200,150
[45] Date of Patent: Apr. 6, 1993

[54] PREPARATION OF GEL-FILLED SEPARATION COLUMNS

[75] Inventor: Donald J. Rose, Jr., Mountain View, Calif.

[73] Assignee: Hewlett-Packard Company, Palo Alto, Calif.

[21] Appl. No.: 722,642

[22] Filed: Jun. 28, 1991

Related U.S. Application Data

[62] Division of Ser. No. 538,348, Jun. 14, 1990, Pat. No. 5,061,355.

[51] Int. Cl.$^5$ .................. G01N 21/00; G01N 31/00; G01N 33/00
[52] U.S. Cl. .................................. 422/62; 422/105; 422/107; 204/200 R
[58] Field of Search .............. 204/182.8, 299 R; 422/62, 105, 107; 264/22

[56] References Cited

U.S. PATENT DOCUMENTS

| | | | |
|---|---|---|---|
| 4,572,819 | 2/1986 | Priddy et al. | 422/62 |
| 4,619,901 | 10/1986 | Webb et al. | 422/62 |
| 4,704,198 | 11/1987 | Ebersole et al. | 204/182.8 |
| 4,790,919 | 12/1988 | Baylor, Jr. | 204/182.8 |
| 4,997,537 | 3/1991 | Karger et al. | 204/299 R |

*Primary Examiner*—John Niebling
*Assistant Examiner*—Caroline Koestner

[57] ABSTRACT

A method of preparing a microcapillary gel separation column for electrophoresis comprises: pretreatment of a tube with a bifunctional reagent to provide polymer bonding sites on the inner wall of the tube; filling the tube with a monomer solution a cross-linking agent, and a photoinitiator; forming a polymer plug by illuminating an initiation section of the tube; growing the plug by moving the tube gradually past the illumination source; and stopping tube motion when the desired length of gal is attained. Provision is made for monitoring polymerization and adjusting tube movement speed to avoid gaps in the growing polymer.

9 Claims, 5 Drawing Sheets

PREPARATION OF GEL-FILLED SEPARATION COLUMNS

CROSS REFERENCE TO RELATED APPLICATION

This is a division of application Ser. No. 07/538,348, filed Jun. 14, 1990, now U.S. Pat. No. 5,061,355.

BACKGROUND OF THE INVENTION

The present invention relates to analytical chemistry and, more particularly, to the preparation of gel columns such as those used in gel electrophoresis. A major objective of the present invention is the formation of a gel column which resists migration of the gel from its container and is essentially free of voids.

Much of recent progress in biotechnology, which holds great promise for advancing medicine and our understanding of life, is predicated on the ability to analyze the constituents of living organisms. In many cases it is necessary to separate constituents, e.g., proteins, to identify them and determine their relative concentrations in a sample.

Gel-column electrophoresis is one important separation methodology. During electrophoresis, an ionic sample is introduced at one end of a gel-filled column. The ionized components migrate longitudinally toward the other end of the column under the influence of an applied longitudinal electric field. The rate of migration for a ion is a function of its charge and bulk. Different chemical species are characterized by different bulks and charges so that they migrate at different rates. Since different species migrate at different rates, they can separate into distinct bands along the column.

The different species can be identified in several ways. In some cases, the final position within the column suffices to identify the chemical species. Similarly, species can be identified by the time at which bands elute from the column. In other cases, the chemical composition of the separated bands can be assessed by a technique such as spectrometry. Alternatively, the gel can be sliced and the bands subject to more intensive analysis.

Gel columns are typically formed by polymerizing a monomer solution in a fused silica tube. The inner wall of the tube is preferably pretreated with a bifunctional reagent. One functional group is capable of bonding to the wall, while the other remains available as a bonding site for the gel. Once the tube is so prepared, monomer solution is introduced and polymerization initiated. The resulting gel is securely bonded to the tube. This bonding resists migration of the gel from the tube during electrophoresis due to charges in the gel from impurities or paritally hydrolyzed monomer functional groups. In addition, bonding minimizes the formation of non-sieving holes near the tube wall that can otherwise occur due to shrinkage that accompanies polymerization. However, shrinkage during polymerization can create voids in the form of air bubbles in the interior of the gel when the bifunctional reagent prevents the gel from separating from the tube wall. These voids disturb the electric fields and the migration of ions through the column, impairing separation.

Precompressing the monomer solution to a density about that of the completed gel prevents shrinkage during polymerization and thus the voids induced by the shrinkage, as taught by Bente and Myerson in U.S. Pat. No. 4,810,456. However, it can be difficult to work with the pressures, preferably around 8200 pounds per square inch, required for precompression. Furthermore, the resulting columns are subject to forming gel inhomogeneities or voids under application of moderate electric field strengths, e.g., 200 volts/centimeter, that can be used during microcapillary gel electrophoresis.

Another approach to forming void-free gel columns involves adding a hydrophillic polymer to the primary monomer solution, as disclosed by Karger et al. in U.S. Pat. No. 4,865,707. The rationale is that the resulting gel is more elastic and therefore more able to accommodate the stresses induced due to polymer shrinkage. However, the admixed hydrophillic polymer can adversely affect constituent separation during electrophoresis. Moreover, this approach has not reliably produced effective separation columns.

What is needed is an improved method and system for preparing electrophoretic gel columns. The method should not require the addition of foreign polymer components which adversely affect gel separation properties. Extreme pressures and other extreme ambient conditions should not be required. The resulting gel should be free of voids and should resist migration even when the higher voltages used for microcapillary electrophoresis are applied.

SUMMARY OF THE INVENTION

In accordance with the present invention, gel formation progresses gradually along the length of a structure, such as a tube, which defines a longitudinally extending channel. The tube is pretreated to promote bonding of the gel-to-be-formed to the inner wall of the tube. A substance including a gel precursor, typically, a monomer solution, is introduced into the tube. A polymer structure, herein called a "plug", is formed or otherwise positioned within an initiation section of the tube. This sections extends only a fraction of the length of the tube, the remainder of the tube remaining essentially devoid of polymer at this point. The plug is then grown to extend over the desired length of the tube. "Growth" herein is used in the sense that it used with respect to crystal growth.

This method can be practiced using a system which comprises a light, or other energy source, and means for moving a tube relative to this light. The tube is pretreated and filled with a monomer solution which includes a photoinitiator, such as riboflavin. The light is directed into the tube near one of its ends until polymer begins to form. After polymerization has begun within the selected section, the tube is moved relative to the light to that polymerization can proceed toward the far end of the tube. Movement is stopped once the desired length of gel is obtained.

Tube movement must not exceed the rate at which the original polymer plug can grow. Otherwise, the "polymer front", i.e., the boundary between the polymer and monomer will fall behind the illuminated region, which moves relative to the tube. In this event, the illuminated region contains only monomer; when polymerized a second gel plug is formed which is separated from the original plug by monomer solution. When the monomer solution in the gap between the gel plugs eventually polymerizes, shrinkage occurs which cannot be relieved by drawing in monomer solution. Accordingly voids can be formed between the locations where plugs were formed.

Accordingly, the system can include a polymerization monitor which monitors polymerization in a portion of the tube that has recently passed the light source. Readings from the monitor are used by a controller to regulate tube speed.

The present invention provides a variety of systems and methods for forming a gel column. The common ingredient is polymerization which progresses longitudinally from a polymer structure in an initiation section of a channel. The progress can be unidirectional, from one end of the tube to the other, or bidirectional, from the middle toward both ends.

Thus a void-free gel column is prepared without using extreme pressures or other extreme conditions. Moreover, empirical tests indicate that columns prepared in accordance with the present invention withstand much greater field strengths than those prepared using precompression. In particular, field strengths as high as 1000 volts/centimeter have been applied without causing gel migration from a microcapillary tube. These and other features and advantages of the present invention are apparent from the description below with reference to the following drawings.

DESCRIPTION OF THE PREFERRED EMBODIMENTS

Figure 1:
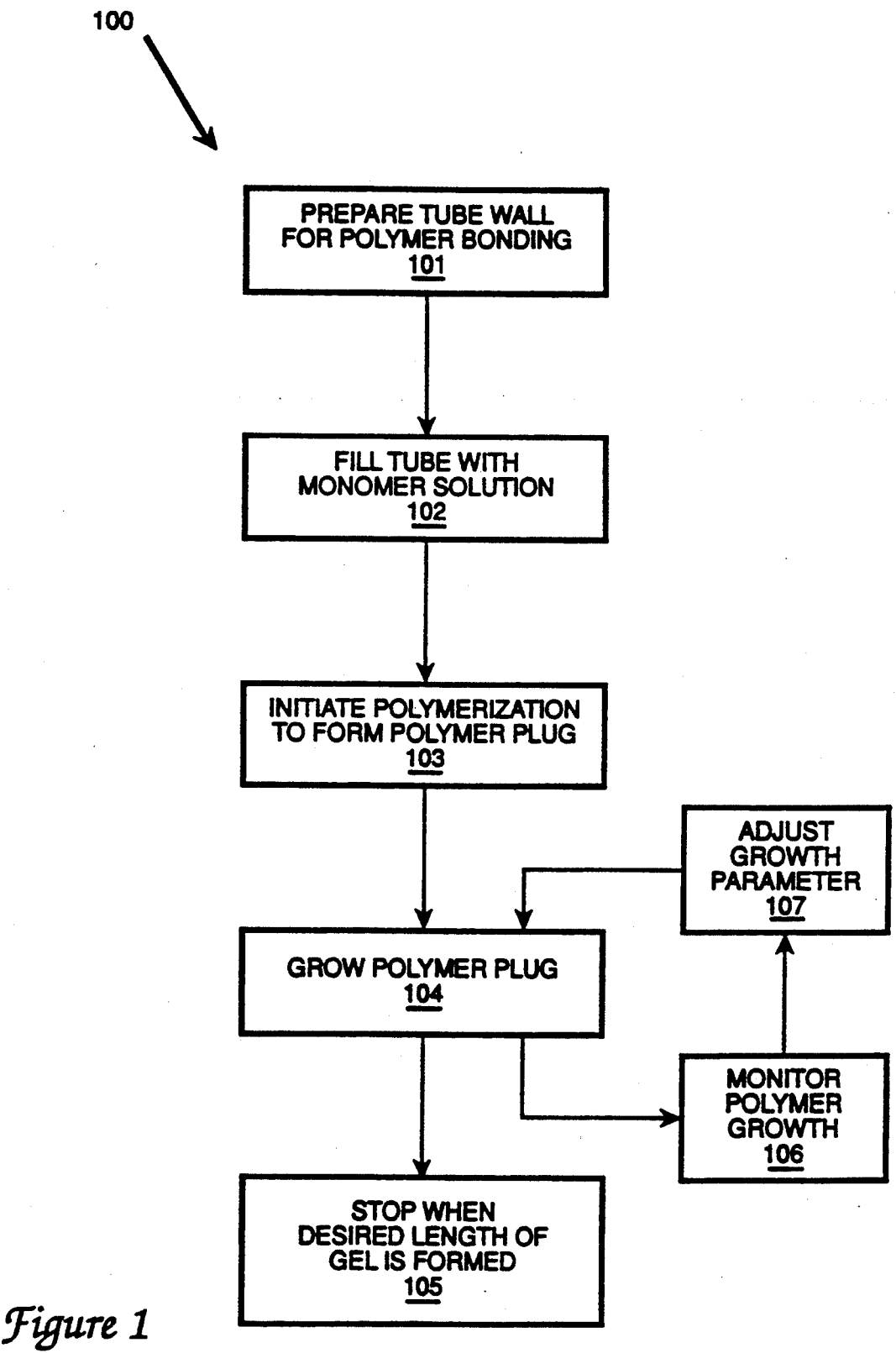
FIG. 1 is a flow chart of a method in accordance with the present invention.

In accordance with the present invention, a method 100 of preparing a microcapillary gel electrophoretic column comprises the steps shown in FIG. 1. The inner wall of a capillary tube is prepared, at step 101, so that a gel to be formed can bond thereto. The tube is filled with monomer solution of step 102. Polymerization is initiated at an "initiation" section of the tube at step 103. A polymer structure is then grown from the initial polymer structure, herein called a "plug", along the length of the tube, at step 104. Promotion of polymerization is stopped, at step 105, when the desired length of gel has been formed. Optionally, polymer growth can be monitored, at step 106 during step 104. If the polymerization is not taking place at an optimal rate, a suitable growth parameter can be adjusted, at step 107.

Figure 2:
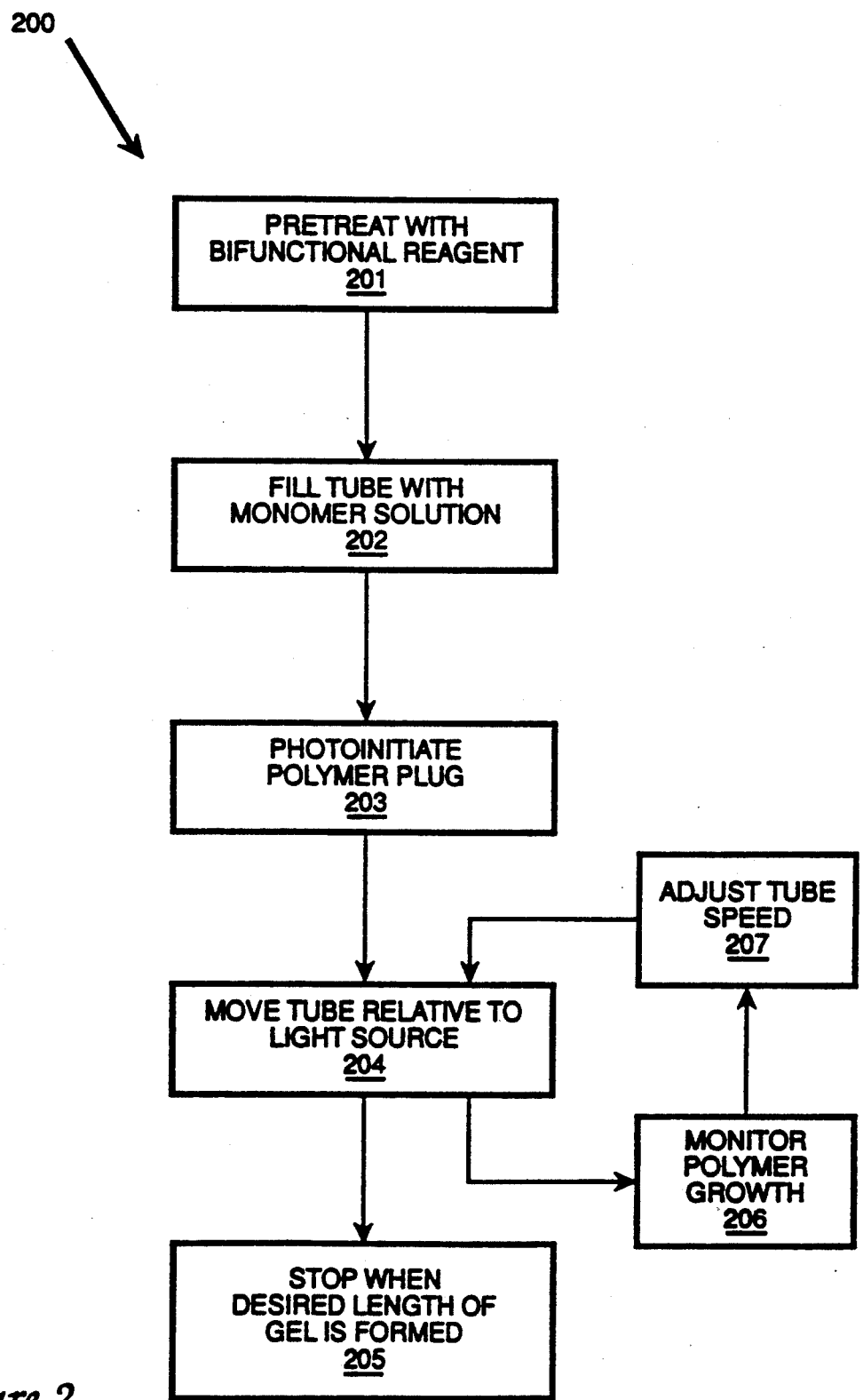
FIG. 2 is a flow chart of a particular implementation of the method of FIG. 1.

A specific implementation of method 100 is presented as method 200 in FIG. 2. At step 201, a bifunctional reagent is applied to the tube walls to provide bonding sites for the gel. The tube is filled, at step 202, with monomer solution including acrylamide, bisacrylamide crosslinker, and riboflavin, a photoinitiator. The solution is exposed to near ultraviolet light at step 203. The light is applied to a small initiation section of the overall tube. This section is toward one end of the tube. The light causes a polymer structure to form only in this section.

The tube is moved relative to the light source in step 204. This promotes polymerization outside of the initiation section. However, polymerization occurs in a spatially ordered manner from the initiation section and longitudinally along the tube. Furthermore, polymerization preferentially involves covalent bonding with the preexisting plug. Consequently, the initial plug grows so that the polymer front remains adjacent the light source. Once polymerization has occurred over the desired length of tube, tube motion can be stopped, as indicated at 205.

Optionally, polymer growth can be monitored at step 206. A light source can be transmitted through the tube behind the polymer front. An appropriate detector can be used to determine the intensity of light transmitted through the tube. The polymer scatters more light than the monomer so that intensity falls as polymerization occurs. Thus, the detected intensity corresponds to the degree of polymerization. If polymerization is occurring too slowly, the motion of the tube can be slowed to ensure gradual progression of the polymerization.

Method 200 is practiced using system 300 which comprises a photoinitiation subsystem 302, a polymerization monitor subsystem 304, and a mechanical subsystem 306. Mechanical subsystem 306 provides for moving a fused silica tube 11 relative to photoinitiation subsystem 302 and polymerization monitor subsystem 304. Photoinitiation subsystem 304 initiates polymerization of monomer solution 13 contained within tube 11. The polymerization causes a polymer plug 15 to grow as tube 11 is moved. Polymerization monitor subsystem 304 monitors the degree of polymerization within tube 11 so that a controller 308 can regulate the rate at which tube 11 moves to optimize throughput and gel quality.

During gel formation, tube 11 is supported between a first reservoir 17 and a second reservoir 19. Reservoirs 17 and 19 contain water to prevent evaporation of water from the tube, i.e., drying of the gel. Tube 11 extends into each reservoir though respectively included silicone rubber septa. Tube 11 and reservoirs 17 and 19 define a tube assembly 21 which is essentially a rigid structure.

Mechanical subsystem 306 comprises a track 310, a rail 312, a rack 314, a pinion 316, and a motor 318. When motor 318 is driven, it rotates pinion 316, which is rigidly coupled to the motor's shaft 320. Pinion 316 engages rack 314, forcing translational movement. Rack 314 is rigidly bonded to rail 312. Thus, from the perspective of FIG. 3, clockwise rotation motor 318 causes rail 312 to move to the left.

The purpose of the leftward movement is to pass the contents of tube 11 sequentially past beams of light (electro-magnetic radiation) provided by photoinitiation subsystem 302. Photoinitiation subsystem 302 comprises a mercury arc lamp 322, a collimating lens 324, a fiber coupler 326, and a pair of optical fibers 328. Optical fibers 328 are held together at their inputs at fiber coupler 326 so they function as a two-fiber optical bundle. The output ends of fibers 328 are locked in position relative to track 310 using fiber optic mount 330. The fiber outputs are secured by mount 330 so that they direct opposing light beams into the adjacent section of tube 11. Thus, leftward longitudinal movement of tube 11 causes light beams from fibers 328 to scan the contexts of tube 11 from left to right.

Mechanical subsystem 306 includes stops 332 to prevent tube assembly 21 from moving rightward relative to rail 312, while the latter is moving leftward. This could otherwise occur if tube 11 drags against mount 330. Mechanical subsystem 306 also includes a microswitch 334 which detects when rail 312 reaches the left end of track 310. A detection is conveyed to controller 308, which then turns off mercury lamp 322 and motor 318.

Initially, tube 11 is filled with monomer solution. Rail 312 and tube assembly 21 are initially at their rightmost positions. Photoinitiation subsystem 302 is activated to initiate polymerization near the left end of tube 11 so that a polymer "seed" or "plug" is formed. Leftward movement of tube 11 causes polymerization to the right of the plug. The speed of motor 318 is set by controller 308. Movement of tube 11 should be fast enough for reasonable throughput and to avoid spontaneous polymerization to the right of mount 330. Tube 11 should move sufficiently slow that monomer gaps longitudinally between polymer sections are minimized. The result should be that polymerization occurs as growth of the plug.

While the speed of motor 318 can be predetermined based on trial and error, system 300 provides for closed loop control of the relative movement of tube 11 and photoinitiation source 302. Polymerization monitor subsystem 304 comprises a tungsten lamp 340, a collimating lens 342, a fiber optic coupler 344, a transmission optical fiber 346, a reception optical fiber 348, a filter 350 and a photosensor 352. Tungsten emits broadband light which is collimated by lens 342. The collimated light is coupled into the input end of fiber 346 via optical coupler 344. The output of transmission fiber 346 is secured by mount 330 at a position to the left or "downstream" of the longitudinal position of the outputs of source fibers 328. The input of reception optical fiber 348 is held by mount 330 at a position opposite that of the output of transmission optical fiber 346. Filter 350, which includes a silicon photodiode, selects out light at wavelengths, around 600 nanometers and filters out stray light from the mercury lamp 322.

The polymer form of the polymerizable substance in tube 11 scatters more light than does the monomer form. Accordingly, the intensity of the light detected by sensor 352 decreases with polymerization. Controller 308 can access the output of sensor 352, and decrease the speed of motor 318 when too little polymerization is occurring, and to increase the speed when polymerization is progressing faster than desired.

System 300 provides for spatially-ordered progressive polymerization. Polymerization occurs as growth at a polymer "front" which tracks the location of the photoinitiation source. This is distinct from prior art "monolithic" gel formation approaches in which polymerization can occur at essentially random positions along the tube. In the prior art, monomer can be left between polymer plugs, both of which try to draw the monomer toward them. The polymer that forms from this monomer is almost inevitably under tension which can result in shrinkage voids.

In the present method, polymerization occurs as growth of a plug. Shrinkage due to polymerization simply draws remaining monomer toward the plug. The tension that could otherwise cause shrinkage voids has little opportunity to accumulate. The end result of the method is a column that has a gel with negligible tension on the polymer molecules. Thus, shrinkage voids are minimized.

Tube 11 is a 30 centimeter (cm) long fused silica capillary with an internal diameter of 100 μm and an outer diameter of 300 μm. Polyimide coating as been burned off except for two centimeters at each end of the tube. The remaining polyimide provides strength where the tube ends extends through the silicone rubber septa of reservoirs 17 and 19.

Tube 11 is pretreated with a bifunctional reagent. This reagent bonds to the inner walls of tube 11 and, in turn, provides bonding sites for polymers. The purpose of the bifunctional reagent is to ensure that the gel-to-be-formed resists migration from the tube when an electric potential is applied during electrophoresis. The bifunctional reagent also minimizes the presence of non-sieving holes near the inner tube wall.

The pretreatment involves filling tube 11 with a 1% by volume solution of 3-acryloxypropyltricholoro silane in toluene. Filling capillary tube 11 is effected by drawing a vacuum from one end while the other end is inserted into the contents-to-be. Tube 11 with a septum attached at one end is simply attached to bottles containing the different fluids to be drawn into the capillary. The reagent is allowed to sit for about ten minutes. Tube 11 is then washed with toluene for five minutes, and then with methanol for five minutes. Tube 11 is then air dried for five minutes.

Figure 3:
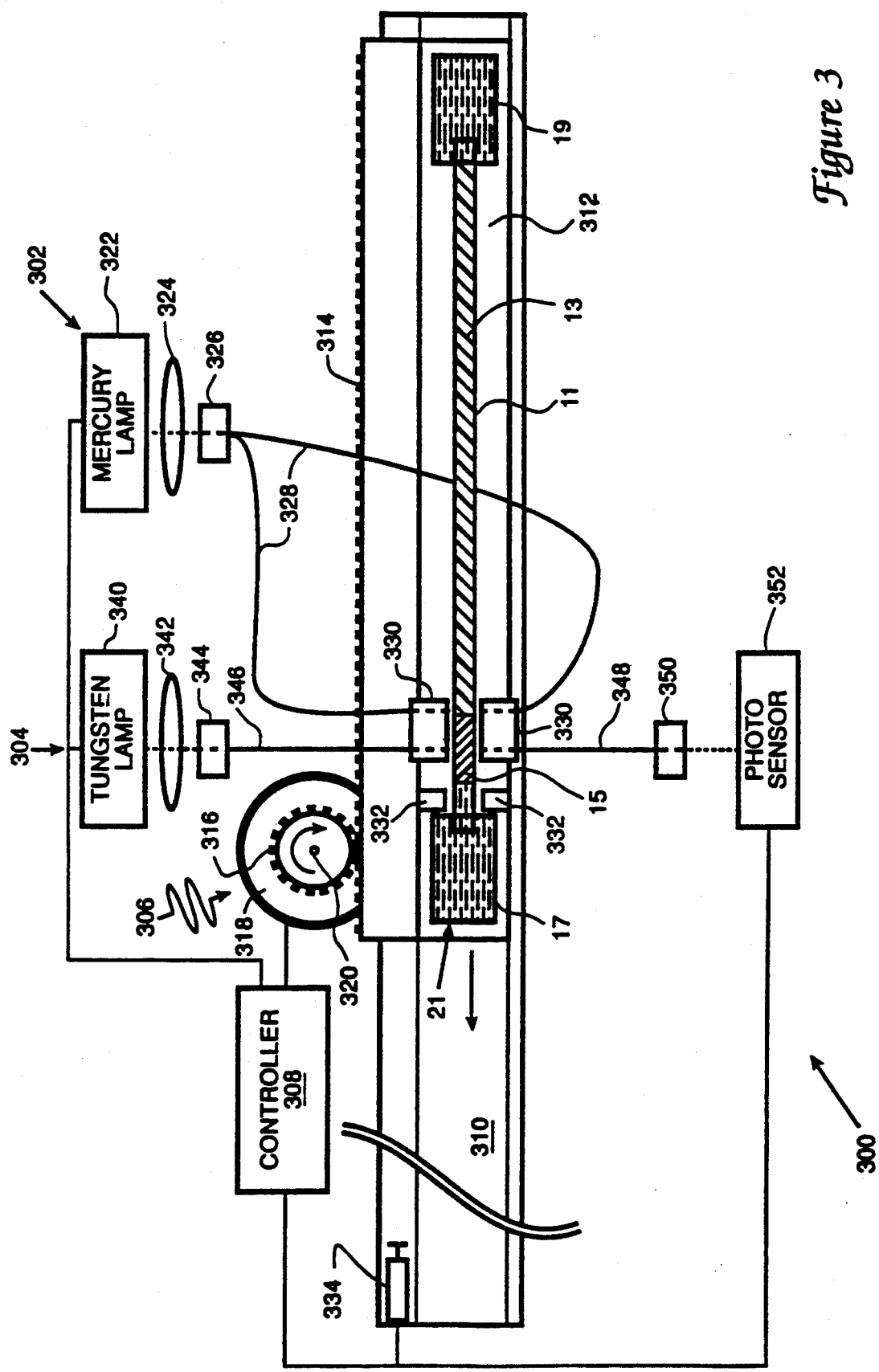
FIG. 3 is a schematic plan view of polymerization system in accordance with the present invention.
Figure 5:
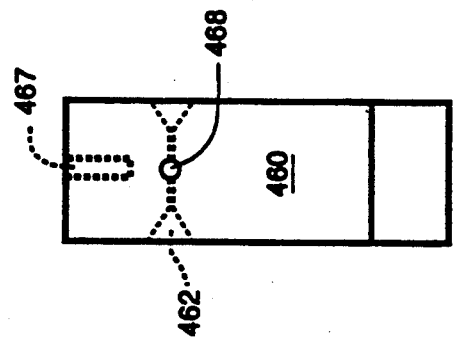
FIG. 5 is a schematic elevational view of the base of a mount of the system of FIG. 3.
Figure 4:
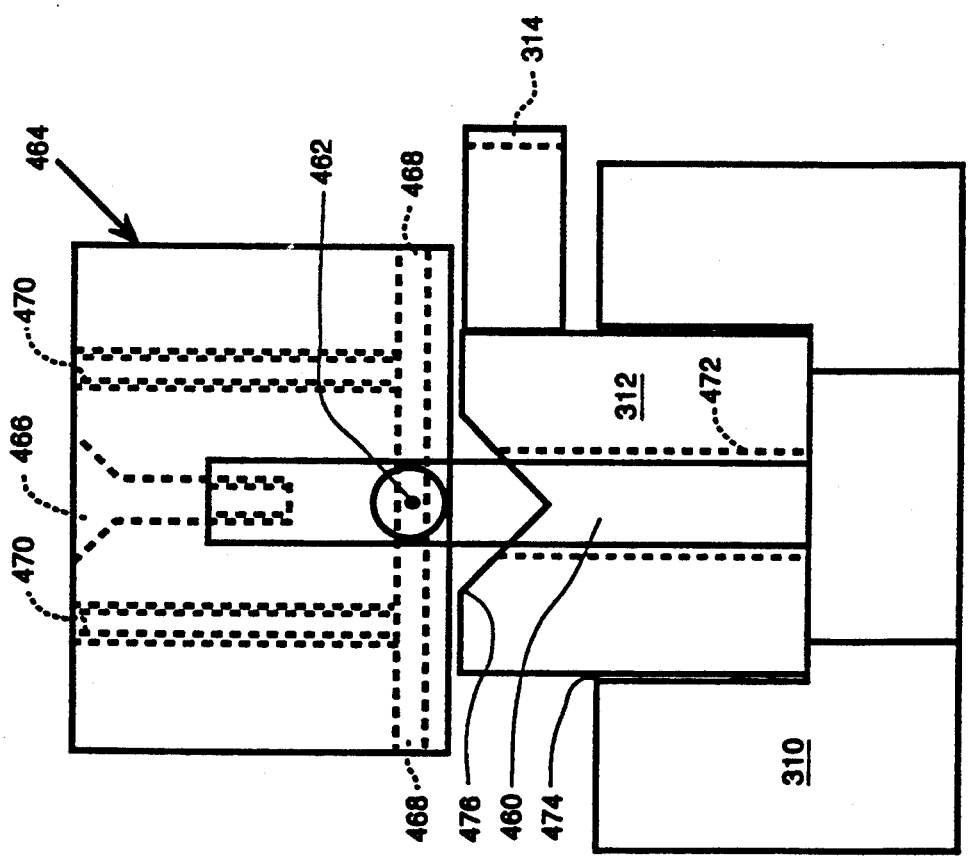
FIG. 4 is a schematic elevational view of parts of the system of FIG. 3.

After pretreatment, tube 11 is filled with monomer solution and is inserted though a base 460 of mount 330 via a hole 462, best seen in FIG. 4. Hole 462 has cones at either end, as shown in FIG. 5, to aid in capturing tube 11 during insertion. This hole has an inner diameter of 500 μm. Septa are place on both ends of tube 11 and then forced into their respective reservoirs 17 and 19. This completes tube assembly 21, as shown in FIG. 3.

The monomer solution includes monomer, a crosslinking agent, a chemical photoinitiator, and a buffer. The concentrations of monomer and crosslinking agent are selected to achieve a desired porosity in the final gel. These concentrations can be expressed respectively as %T and %C where $$\%T = \frac{\text{grams of acrylamide} + \text{grams of bisacrylamide}}{100 \text{ milliliters of solvent}}$$

$$\%C = \frac{\text{grams of bisacrylamide} \times 100}{\text{grams of bisacrylamide} + \text{grams of acrylamide}}$$

The monomer solution used in tube 11 is 10 %T and 2.6 %C. The concentration of riboflavin is about $10^{-5}$ molar (M). When riboflavin molecules absorb photons of the near ultraviolet wavelengths (400-500 nanometers) emitted by mercury lamp 322, they are excited and become free radicals. The free radicals initiate polymerization both by directly interacting with monomer and by generating intermediate radicals from water molecules. The buffer is 2 millimolar sodium phosphate pH 7 buffer. A catalyst, such as TEMED (tetraethylenemethylenediamine) can be added to facilitate polymerization, provided polymerization remains gradual.

The vacuum is removed and the free end inserted through another septum which is fitted snuggly into the top of reservoir 17 which contains water. The reservoir containing monomer is replaced with reservoir 19 containing water.

Once tube assembly 21 is in place, a cap 464 for mount 330 is screwed on; i.e., a screw is engaged within countersunk hole 466 in cap 464 and threaded hole 467 in base 460, shown in FIG. 5. Optical fibers 328 from mercury lamp 322 are inserted in lateral holes 468 on either side of cap 464. Each fiber 328 is inserted until it touches tube 11. Then the fiber is withdrawn until light can be seen between tube 11 and the fiber when looking down capillary hole 462. This procedure should yield a spacing of about 0.2 to 0.5 millimeters between tube 11 and fibers 328. Fibers 328 have a core of about 600 μm. The fibers are sheathed in stainless steel for rigidity and have an outer diameter of about 1500 μm. Holes 462 have inner diameters of about 1800 μm. For each fiber 328, once the desired spacing has been achieved, it is held in place by tightening a screw disposed in a respective hole 470 in cap 464. Sensor fibers 346 and 348 are similarly installed using holes in cap 464 two to ten millimeters downsteam (left in FIG. 3, toward the reader in FIG. 4) of those used for fibers.

As indicated in FIG. 4, base 460 of mount 330 extends through an 18 cm elongated slot 472 in rail 312. Slot 472 is at least as long as the desired length of the eventual gel column. In this case, a 15 cm gel column is to be formed from thirty-inch tube 11. Rail 312 is seated within a square groove 474 of track 310. Rail 112 has a V-shaped groove 476 to accommodate tube 11. Rack 314 is metal, while track 310, rail 312, and pinion 316, of FIG. 3, are polycarbonate.

Rail 312 begins at its rightmost travel position, with reservoir 17 just to the left of mount 330, from the perspective of FIG. 3. Mercury lamp 322 remains on until polymerization is established in the section of tube 11 near the output ends of fibers 328. Polymerization can be presumed by the passage of a certain amount of time, or detected visually or using monitor subsystem 304. Once polymerization has begun, motor 318 can drive tube 11 to the left at a rate selected or controlled to promote gradual growth at the polymer plug front which is advancing rightward relative to tube 11 and is preferably stationary relative to mount 330.

Once the middle 18 cm of tube 11 are exposed to photoinitiation, as indicated by activation of microswitch 334, controller 308 switches mercury lamp 322 and motor 318 off. Tube 11 is left in place for sufficient curing to take place so that the column can be handled without disturbing the gel. Once curing is complete, about 7.5 cm are cut from either end of tube 11 to yield the desired gel filled column.

Figure 6:
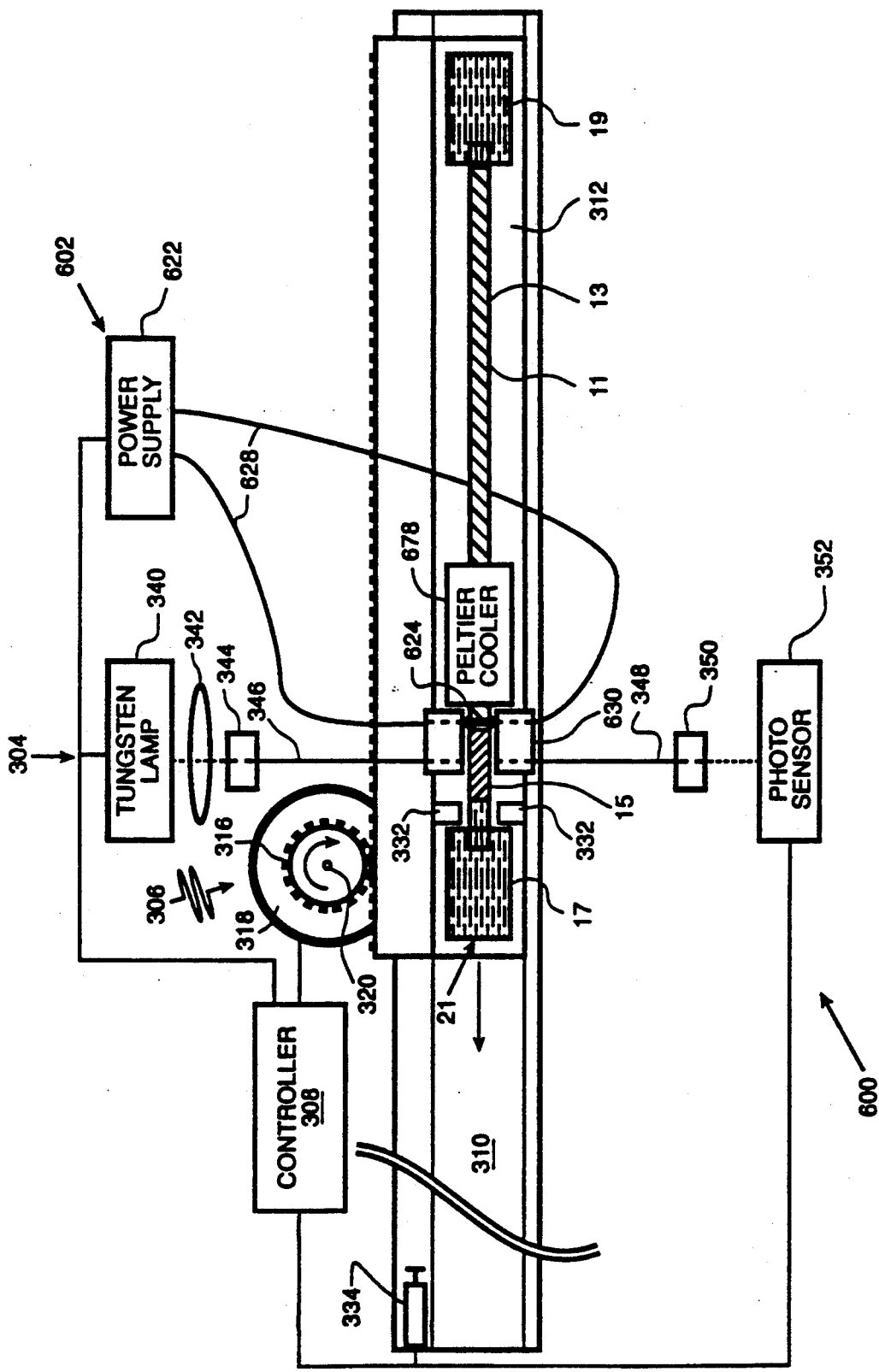
FIG. 6 is a schematic plan view of an alternative polymerization system in accordance with the present invention.

An alternative system 600 for preparing a microcapillary gel electrophoretic column, shown in FIG. 6, uses heat rather than light to initiate polymerization. System 600 is a modification of system 300 so like parts are assigned like reference numerals. A thermal initiation sub system 602 replaces photoinitiation subsystem 302. Removed components include mercury lamp 322, source collimating lens 324, fiber coupler 326, and source fibers 328. In their place are a power supply 622, a nichrome resistive heating element 624, and leads 628 between power supply 622 and heating element 624. A modified mount 630 is used to accommodate leads 628 and heating element 624. In addition, a peltier cooling element 678 leads heating element 624 along tube 11 to minimize polymerization due to conduction of heat to the right of heating element 624.

The monomer solution can be similar except that a thermal initiator rather than a photoinitiator is used. A $10^{-2}$ to $10^{-4}$ molar concentration of ammonium persulfate is used in place of the riboflavin used with system 300. Once again, a catalyst such as TEMED can be added to increase the rate of polymerization if desired.

The present invention provides for a variety of alternatives to the embodiments described above. Tubes of different inner diameters are provided for. For example, the invention applies to the manufacture of microcapillary columns with inner diameters between 25 μm and 500 μm. In addition, it can apply to non-capillary columns with diameters between 0.5 to 5.0 mm. Other column inner diameters can also be accommodated. Moreover, different lengths are provided for. The invention provides for columns 50 mm to 500 mm long.

The method can be applied to any elongated means for defining a channel in which gel is to be formed. Some embodiments prepare elongated grooves and plates with gels. Column cross sections which are square, rectangular, flat, circular and other shapes are within the scope of this invention. The resulting product can be used for electrophoresis or other applications for elongated structures with gels. Preparation of the channel can involve binding bifunctional reagents, which, as used herein, include reagents with two or more functional groups. Where appropriate, the preparation can involve cleaning or abrading a channel wall.

In the preferred embodiments, a monomer served as the precursor for the gel. However, the precursors need not be monomers nor need they be in solution. Oligomer precursors are utilizable, for example. Generally, the tube should be filled with a substance bearing a polymerizable gel precursor.

As indicated above, photoinitiation and thermal initiation can be used to begin polymerization. Other forms of energy can also be used including X-rays, gamma rays, particle rays, magnetic fields, ultrasound, etc. A chemical responsive to the form of energy used can be used as an intermediate radical source, just as riboflavin is used in photoinitiation. Alternatively, a chemical intermediary can be omitted if the energy can from radicals from the gel precursor directly.

In some embodiments, initiation does not require a radiant energy source. For example, a polymer plug with free radicals can be introduced through one end of the tube. In this case, the polymer plug can be introduced either before or after the monomer is drawn into the tube. Alternatively, initiator or facilitator can be introduced at only one end of the tube. The requirement is that a polymer structure be formed in one section which extends only a fraction of the length in which gel is to be formed, while the remainder of the tube is essentially free of polymer.

Where polymer is not formed is as important as where it is formed. The advantages of the present invention arise from plug growth. If the initial plug is as long as or nearly as long as the tube itself, longitudinal growth will be negligible. The initial plug should be at most one-quarter the length of the tube. Generally, the initial plug is less than 10% of the tube length. Moreover, if multiple plugs are formed, monomer solution cannot fill the voids left as monomer trapped between plugs polymerizes. Hence, polymerization should be avoided except within the initiation section and at the plug front.

Once the initial polymer structure is formed, it can serve as a seed which can grow by bonding with nearby monomer molecules. In the preferred embodiments, polymerization progresses by moving the tube relative to the same source used for initiation. However, in some embodiments a energy source different from the one used during initiation can be used for progressive polymerization. For example, photoinitiation can be followed by heat-supported progressive polymerization.

Under particular circumstances polymerization can occur at the polymer front without additional localized energy introduction. In such a case, an initiator source can be turned off and polymerization allowed to proceed. Alternatively, external energy can be applied to support progressive polymerization after physical introduction of a polymer seed structure. In further alternatives, polymerization progresses due to progression of a factor affecting polymerization. For example, heat conducted by a tube can be used to promote longitudinally progressive polymerization, likewise, diffusion of an originally localized chemical initiator or facilitator can promote longitudinally progressive polymerization.

In the preferred embodiments, the tube is moved past a localized energy source to promote progressive polymerization. Alternatively, the source can be moved past a stationary tube. Movement can be virtual as well as physical. For example, the heat or light source can be a linear array of diodes. Source movement is effected by selection of the diodes to be activated at any given time. Similarly, a liquid crystal shutter can be used to select which sections of a tube are exposed by a light source. In other embodiments, a tube moves into, rather than past, an energy source. The source can be a heat or light tunnel. A tube can be gradually inserted into the tunnel so that energy continues to be fed into sections of tube introduced into the tunnel. This approach can be preferred where polymerization behind the wavefront needs energy support to complete polymerization or curing. In embodiments in which polymerization progresses without local energy introduction, there is no relative movement.

As described above, polymerization can be initiated near one end of the tube and polymerization progressed toward the other end. Some embodiments employing virtual movement of an energy source and some not requiring a localized energy source to support polymer growth permit initiation near the longitudinal center of the tube. Polymerization then progresses toward both ends at once. A energy source, such as a photo-diode array, capable of virtual movement can be made to operate so that two opposing illumination sequences drive polymerization toward both ends of a tube at once. "Virtual" movement refers to apparent movement caused by activating and deactivating energy sources in sequence.

Monitoring polymerization is optional. Monitoring can be based on scattering or any other characteristic capable of monitoring and distinguish a given polymer from its precursor. The feedback can be used for real-time control of progressive polymerization. In embodiments with a localized or tunnel energy source, feedback can be used to adjust the speed of the relative movement of tube and source. In addition to adjusting speed, or instead of moving speed, other polymerization rate parameters can be adjusted. For example, temperature, ambient light, concentration of chemical initiator or facilitator, can be adjusted. Some of these variable are suitable for closed-loop regulation. Others are more suitable to trial and error methodology in which the results of one run are used to determine the settings for the next. These and other variations upon and modifications to the described embodiments are provided for by the present invention, the scope of which is limited only by the following claims.

I claim:

1. A system for polymerization of a material in a tube comprising:
    holding means for holding a longitudinally extending tube assembly including said tube;
    an energy source capable of directing energy into an initiation section of said tube to the exclusion of other sections of said tube;
    redirection means for progressively changing the section of said tube into which said source directs radiation;
    monitor means for monitoring the progress of polymerization in said tube; and
    control means for controlling the rate of redirection relative to said tube in response to the as-monitored progress of polymerization in said tube, said control means being coupled to said first monitor means and said redirection means.

2. A system as recited in claim 1 wherein said energy source includes an optical fiber along which electromagnetic radiation can be directed to and through a wall of said tube.

3. A system as recited in claim 2 wherein said monitor means includes a source of electromagnetic radiation including at least one characteristic wavelength not significantly radiated by said energy source, said monitor means including filter means for selectively passing said characteristic wavelength.

4. A system as recited in claim 1 wherein said energy source generates heat from a nichrome resistive heating element.

5. A system as recited in claim 1 further comprising evaporation minimizing means for minimizing evaporation of said material in said tube.

6. A system as recited in claim 5 wherein said energy source radiates electromagnetic radiation via an optical fiber and through a wall of said tube.

7. A system as recited in claim 6 wherein said monitor means includes a source of electromagnetic radiation including at least one characteristic wavelength not significantly radiated by said energy source, said monitor means including filter means for selectively passing said characteristic wavelength.

8. A system as recited in claim 5 wherein said energy source generates heat from a nichrome resistive heating element.

9. A system as recited in claim 1 further comprising a fluid reservoir disposed for receiving an entrance of said tube so that during said polymerization monomer solution can be drawn away from said entrance and toward a polymer front in said tube.

* * * * *